United States Patent
Murphy

[11] Patent Number: 5,951,592
[45] Date of Patent: Sep. 14, 1999

[54] APPARATUS AND METHOD FOR APPLYING ANTITACHYCARDIA THERAPY BASED ON VENTRICULAR STABILITY

[75] Inventor: Anthony Murphy, Dulwich Hill, Australia

[73] Assignee: Pacesetter, Inc., Sylmar, Calif.

[21] Appl. No.: 08/975,308

[22] Filed: Nov. 21, 1997

[51] Int. Cl.⁶ .................................................. A61N 1/39
[52] U.S. Cl. ............................... 607/4; 607/14; 600/518
[58] Field of Search ........................ 607/4, 5, 9, 14; 600/515, 518, 519, 521

[56] References Cited

U.S. PATENT DOCUMENTS

| | | | |
|---|---|---|---|
| 4,880,005 | 11/1989 | Pless et al. | 607/15 |
| 5,205,283 | 4/1993 | Olson | 607/4 |
| 5,350,406 | 9/1994 | Nitzsche et al. | 607/14 |
| 5,462,060 | 10/1995 | Jacobson | 128/702 |
| 5,591,215 | 1/1997 | Greenhut et al. | 607/14 |
| 5,620,471 | 4/1997 | Duncan | 607/9 |

*Primary Examiner*—William E. Kamm
*Assistant Examiner*—Kennedy J. Schaetzle
*Attorney, Agent, or Firm*—Gottlieb, Rackman & Reisman, P.C.

[57] ABSTRACT

An implantable cardioversion/defibrillation device includes a cardioversion signal generator and a defibrillator signal generator. Heart beat rates are classified into a first, an intermediate and a second range. A ventricle state determinator is also provided to determine the current status of the ventricle. At the low and high rates cardioversion and fibrillation signals are generated and applied to the heart, respectively. At the intermediate rate, if the ventricle is stable, cardioversion signals are generated and applied. If the ventricle is unstable, then defibrillation signals are applied. Ventricle stability is determined from the variability of the ventricular rate.

17 Claims, 2 Drawing Sheets

APPARATUS AND METHOD FOR APPLYING ANTITACHYCARDIA THERAPY BASED ON VENTRICULAR STABILITY

BACKGROUND OF THE INVENTION

A. Field of Invention

The subject invention pertains to implantable cardioversion devices, or ICDs, and more particularly, to an ICD with means for applying antitachycardia therapy based on both ventricular rate and stability. The term 'ICD' is used generically herein to cover implantable devices capable of providing antitachycardia therapy, including both cardioversion and defibrillation therapy. These devices may include means for providing bradycardia therapy as well.

B. Description of the Invention

Implantable cardioverison devices of the kind described above are used to provide therapy to a patient having faster than normal, often irregular heart rhythms. One such device of this type is described, for example, in U.S. Pat. No. 5,191,884, incorporated herein by reference.

Typically, in such devices, the intrinsic cardiac activity in the ventricle is monitored to detect an abnormal ventricular heart rate. It is customary to classify this heart rate into three ranges: normal, fast and very fast. Of course, for cardiac activity in the normal range, no therapy is required. For fast ventricular rate, antitachycardia (ATP) pacing may be applied. This may consist, for example, of applying pacing pulses to the heart at a rate slightly faster than the sensed VT rate (orthorhythmic pacing).

A problem with present devices is that they rely on the intrinsic ventricular rate to determine what kind of therapy to apply. However, a heart exhibiting what appears to be a ventricular rate near the border between the fast and very fast rate may not respond necessarily favorably to ATP and may require defibrillation therapy (ST). In fact, in some cases, if ST is required, ATP may cause the ventricular rate to rise even higher, and therefore it would take a longer time to stabilize the heart. There are a number of situations in which it is undesirable to apply ATP. One of these is the situation where sensing errors produce an unreliable rate estimate, causing inappropriate orthorhythmic pacing rate. Others are polymorphic ventricular tachycardia, and ventricular fibrillation.

A solution to some of these problems is attempted in U.S. Pat. No. 5,462,060. This patent discloses a dual chamber system in which interval and stability criteria are used in both cardiac chambers, as well as the PR interval to distinguish VT from arrhythmia of atrial origin, such as sinus tachycardia, atrial tachycardia, atrial flutter, atrial fibrillation, etc. These criteria are used in a complex algorithm to classify arrhythmia, while the present invention is directed toward choosing the correct therapy itself.

OBJECTIVES AND SUMMARY OF THE INVENTION

In view of the above disadvantages of the prior art, it is an objective of the present invention to monitor a single chamber of the heart, preferably the ventricle and to determine therefrom the proper therapy to be applied.

A further objective is to provide an ICD which is more successful in treating VT than previous ICDs.

Another objective is to reduce the incidence of acceleration caused by application of orthorhythmic ATP with incorrect Tachycardia Cycle Length (TCL) estimate.

It is a further objective to safely allow ATP at cycle lengths as short as 200 ms, without risking inappropriate therapy for ventricular fibrillation.

Yet a further objective is to reduce delay to shock therapy caused by application of ATP to polymorphic VT or VF.

Other objectives and advantages of the invention shall become apparent from the following description. Briefly, an ICD constructed in accordance with this invention includes a ventricular sensor for sensing a ventricular intrinsic rate. This rate is classified, based on current value and past history, into a normal, fast, intermediate and very fast range. The normal, fast and very fast ranges are treated in the usual manner, discussed above. For the intermediate range, a ventricular monitor determines if the ventricle is relatively stable. For a stable ventricle ATP is applied just like for the fast range. For an unstable ventricle ST is applied just like for the very fast rate.

DETAILED DESCRIPTION OF THE INVENTION

Figure 1:
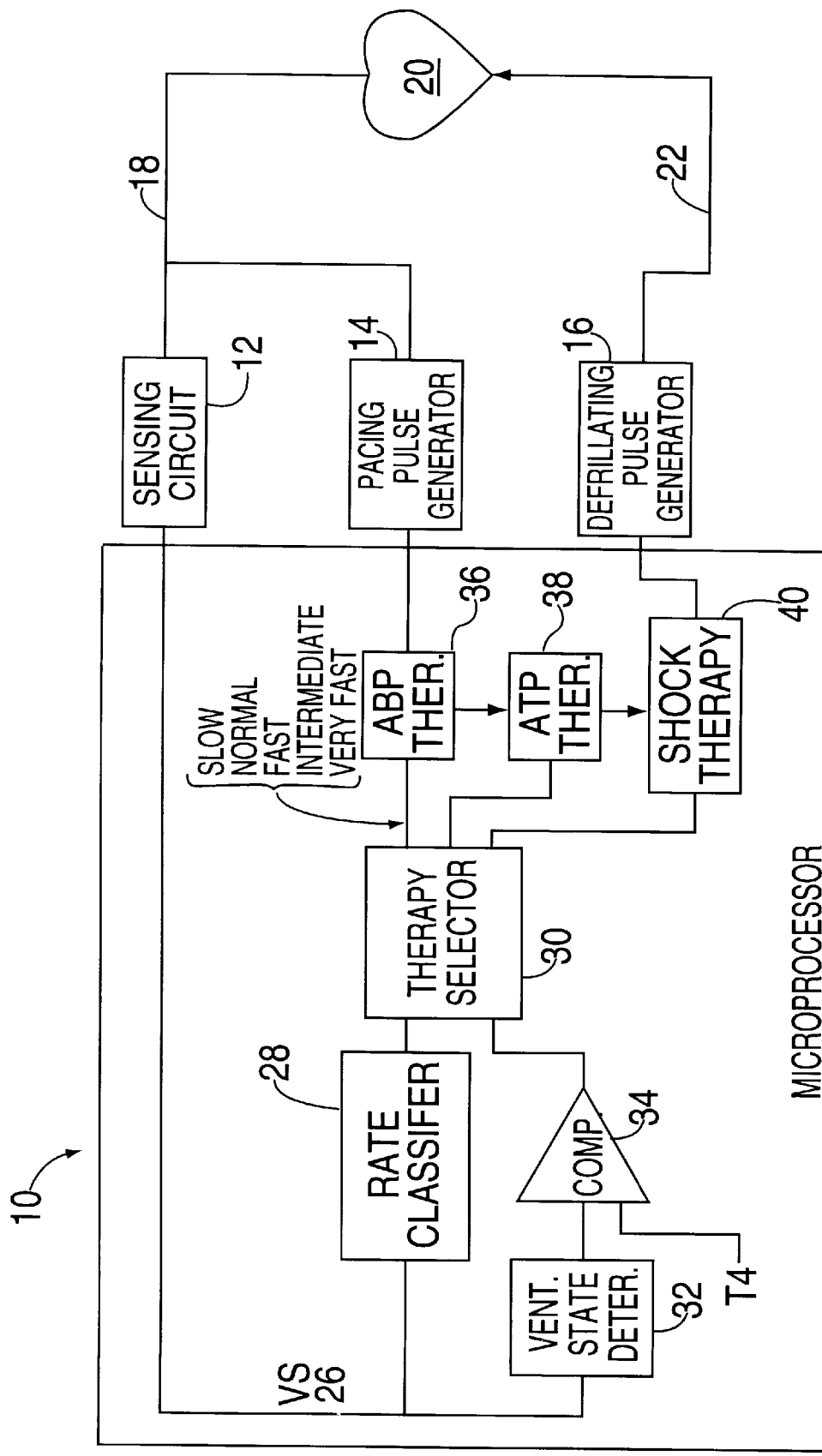
FIG. 1 shows a block diagram for an implantable cardiac device constructed in accordance with this invention.

Referring now to FIG. 1, a device 10 constructed in accordance with this invention, includes a sensing circuit 12, a pacing pulse generator 14 and a defibrillating pulse generator 16. Sensing circuit 12 and pacing pulse generator 14 share a lead system 18 of two or more electrodes (not shown) extending into the ventricle and, optionally, the atrium of a heart 20. The sensing circuit senses intrinsic cardiac activity in the cardiac chamber or chambers (depending on whether the device 10 is a single or dual chamber device). Pacing pulse generator 14 generates pacing pulses for the cardiac chamber in accordance with a specific cardiac therapy to be applied, as shall be discussed in more detail below.

Defibrillating pulse generator 16 is used to generate defibrillation pulses. Since these defibrillation pulses have a much higher energy level than pacing pulses they are normally applied externally by defibrillating electrodes (not shown). Accordingly, a separate lead system 20 is used for delivering these later pulses to the heart.

Device 10 further includes a microprocessor 24 provided for monitoring the cardiac signals from heart 20 and for generating commands to the pacing pulse generator 14 and defibrillating pulse generator 16. For this purpose the microprocessor 24 includes a ventricular rate classifier 28 receiving a signal VS 26 from the sensing circuit 12 and indicative of ventricular intrinsic activity and a therapy selector 30. The ventricular rate classifier 26 classifies the ventricle based on the ventricular rate signal into one of several categories, as described more fully below.

The ventricular sense signal VS 26 (and/or other signals such as an atrial sense signal indicative of atrial cardiac activity) is also provided to a ventricular state determinator 32 provided to selectively determine whether the ventricular contractions are relatively stable or chaotic. For this purpose, the determinator 32 generates an output indicative of the state of the ventricle. This signal is fed to a comparator. The comparator 34 compares this signal to a threshold level TH. The results of the comparison are also fed to the therapy selector 30.

Based on this information, the therapy selector 30 then selects an appropriate therapy. Three circuits 36, 38 and 40 are provided to generate appropriate commands to the pacing or defibrillator pulse generator 14, 16, respectively. More specifically, the selector 30 activates circuit 36 for generating antibradycardia pacing (ABP) therapy, circuit 38 may be used to provide antitachycardia pacing (ATP) therapy and circuit 40 is used for generating defibrillation (i.e., shock) therapy (ST). These circuits receive other signals such as the ventricular sense signal 26, atrial sense signal (not shown) and others. Typically, these circuits may be state engines generating in response commands to the pulse generators 14, 16 at appropriate times. Such circuits are well known in the art and need not be described in more detail herein.

The components shown within the microprocessor 24 are shown as discrete components for the sake of clarity. However, it should be understood that they are preferably implemented by software.

Figure 2:
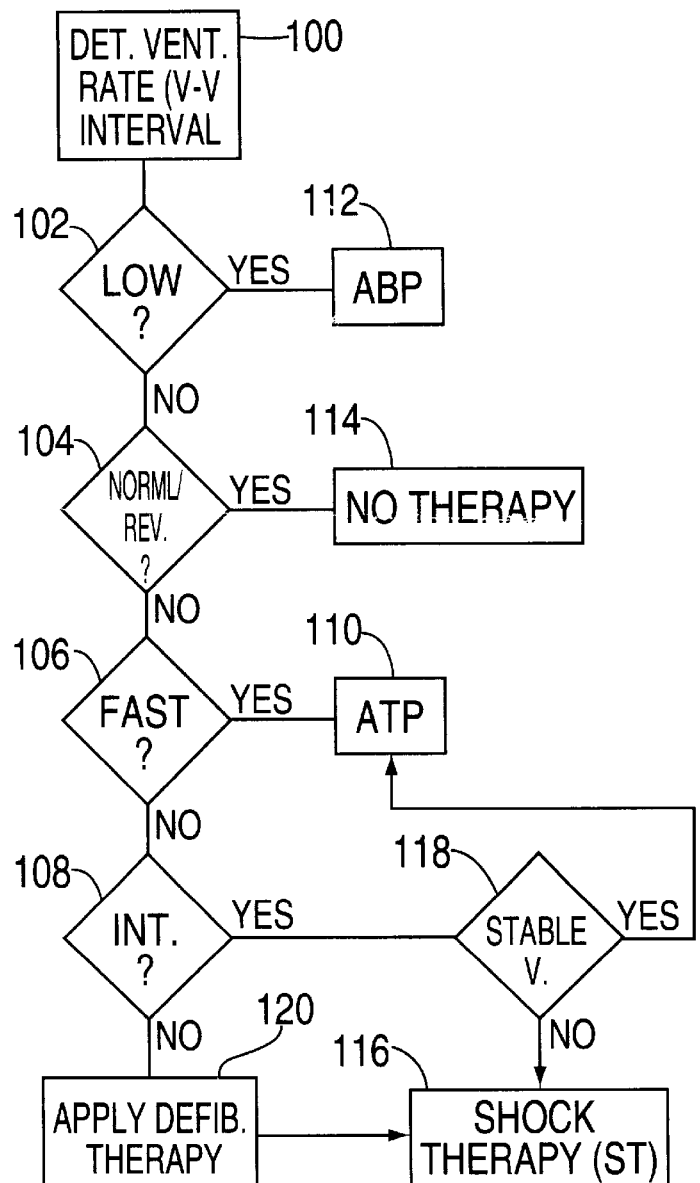
FIG. 2 shows a block diagram for the operation of the device of FIG. 1.
Figure 3:
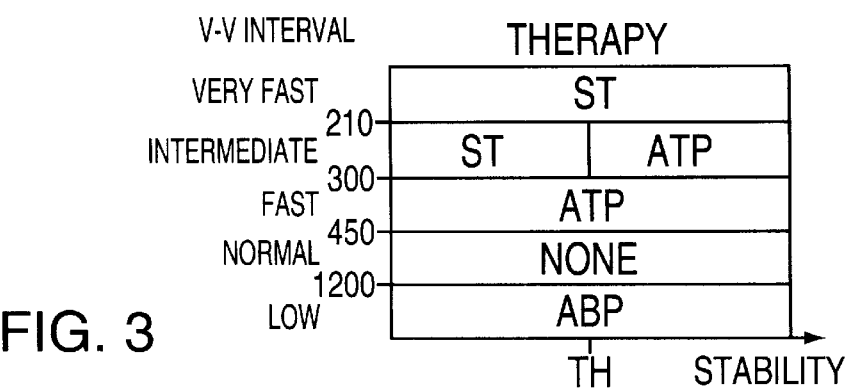
FIG. 3 shows a graph illustrating the different modes of operation for the device in relation to the intrinsic ventricular pacing rate.

The operation of the device 10 shall now be described in greater detail in conjunction with FIGS. 2 and 3. Starting in FIG. 2 with step 100, a ventricular event is sensed by sense circuit 12 and a ventricular rate (or more properly a V—V interval) is calculated from the preceding such event and sent to rate classifier 28. Classifier 28 then determines if this ventricular rate is low (step 102), normal (step 104), fast (step 106) or intermediate (step 108). As shown in FIG. 3, these ranges may be defined as follows:

| Rate (msec) | Classification |
|---|---|
| >1200 | Low |
| 450–1200 | Normal |
| 300–450 | Fast |
| 210–300 | Intermediate |
| <210 | Very fast |

The appropriate classification is provided to therapy selector 30 which in response selects an appropriate therapy (if any). Thus, as shown in FIGS. 2 and 3, for a low rate, antibradycardia pacing (ABP) may be selected (step 112) (circuit 36).

For a normal rate, no therapy is selected (step 114). It will be understood by one skilled in the art that these are gross oversimplifications of these features which do not play an important part for the present invention, and have been included only for the sake of completeness. In fact, the first step (ABP therapy) may be optional. It is well known in the art that these determinations normally are made using much more sophisticated criteria which do not form a part of this invention.

Additionally, it should be noted that this invention is not restricted at steps 104, 106 or 108 strictly to a simple comparison to classify the ventricular activity, but other criteria may be used as well. For example, in step 104 if out of previous, let us say ten ventricular beats, a large number (such as five) is found to be at or near normal rate, while the other rates were below 400 msec, then a determination can be made that the ventricular rate is normal. Similarly, steps 106 and 108, a preselected number of events out of a total number (preferably over 50%) for example, 6 of 10, events must exceed the predetermined limits before a decision is made that the ventricle is beating at a higher rate than normal rate.

In any event, if in step 106, the classifier 28 determines that the heart should be classified as having a fast ventricular rate, then in step 110 the ATP circuit is activated and ATP therapy is applied to the heart. See FIG. 1 (circuit 38).

Importantly, in step 108, if the classifier 28 classifies the ventricle as beating at an intermediate rate as determined in step 108, then in step 118 classifier 28 performs a test to determine if the ventricle is stable. This determination may be done in a number of different ways such as determining the ventricular rate variability by the difference between two entries in an ordered list of the last N ventricular events. (For example, the difference or ratio between every third and seventh intervals in an ordered list of the last ten intervals may be compared). Alternatively, a mean absolute difference between the last N ventricular intervals may be calculated. A third approach is to determine the standard deviation of the last N ventricular events. In order to perform any of these functions, recent ventricular events are entered into ventricular state detector 32 which performs the required stability determination as discussed, the variability of VS.

The resulting value is a quantitative indication of the stability of the ventricle. This variability value is then entered into a comparator 34 and compared to a preselected threshold level. The output of the comparator 34 is fed to the therapy selector 30. At an intermediate ventricular rate, therefore, the therapy selector monitors the ventricular state detector 32 and comparator circuit 34. If the ventricle is stable, then no shocks are necessary and the patient receives instead ATP therapy.

If however, in step 118 it is found that the ventricle is unstable, i.e., comparator 34 finds that the ventricle stability is lower than the threshold value TH then instead fibrillation therapy (DT) is applied, i.e., defibrillation shocks are generated and applied to the heart through electrode 22 by circuit 40 (step 116). This operation is shown graphically in FIG. 3.

Finally, at a very fast rate, higher than the intermediate rate as determined by the classifier 32 in step 108, defibrillation therapy DT is applied by circuit 40.

In this manner, the apparatus shown in the Figures classifies the state of the ventricle and provides appropriate therapy in a relatively fast manner.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable cardioversion/defibrillation device comprising:

a cardiac sensor for sensing a heart beat;

a categorizer for categorizing said heart beat into a first rate and a second rate;

a first generator for generating first therapeutic signals;

a second generator for generating second therapeutic signals, said first and second therapeutic signals being selected to provide corresponding therapy to the patient;

a ventricular stability detector for sensing that the ventricle is stable based on the variability of sensed ventricular intervals and for generating a stable ventricle signal; and a controller for generating one of a first and a second command for activating said first and second generators respectively, said first command being generated when said first rate is indicated and when said second rate is indicated in the presence of said stable ventricle signal, and said second command is generated in the absence of said stable ventricle signal;

wherein said categorizer defines a first heart rate range, a second heart rate range and a third heart rate range, said second heart rate range being disposed between said first and third ranges, and wherein said first rate is in said first heart rate range and said second rate is in said second heart rate range; and wherein said controller generates said second command when said heart rate is in said third heart rate range.

2. The device of claim 1 wherein said first therapeutic signals are antitachycardia pacing signals and said second therapeutic signals are shock signals.

3. An implantable cardioversion/defibrillation device comprising:

a sensing circuit for sensing a heart rate in a cardiac chamber;

a rate classifier for defining at least a first heart rate range, a second heart rate range and a third heart rate range, said heart rate ranges being adjacent;

a ventricle state determinator for determining a variability of the ventricular rate, said determinator generating a stability signal when said variability is below a threshold;

a pulse generator for generating antitachycardia pulses in response to an antitachycardia pacing command;

a shock generator for generating shock pulses in response to a shock command;

a command generator for generating said antitachycardia pacing command in response to a heart rate in said first range and to said heart rate in said second range in the presence of said stability signal, and said shock command in response to said heart rate in said second range in the absence of said stability signal and to said heart rate in said third range.

4. The device of claim 3 wherein said rate classifier further defines a fourth range below said first range.

5. The device of claim 4 wherein said pulse generator generates pacing pulses in response to said heart rate in said fourth range.

6. The device of claim 5 wherein said pulse generator generates said pacing pulses in response to a pacing command, and wherein said controller generates said pacing command in response to said heart rate in said fourth range.

7. The device of claim 5 wherein said command generator is adapted to generate commands for pacing pulses defining one of an antitachyarrhythmia and an antibradycardia therapy.

8. An implantable cardiac device comprising:

a ventricular sensor that senses ventricular intrinsic rate;

a categorizing circuit that analyzes said ventricular intrinsic rate as one of a fast rate range if said ventricular intrinsic rate is between a first and a second threshold, a very fast rate range if said intrinsic ventricular rate is between a third and fourth threshold and an intermediate rate range if said intrinsic ventricular rate is between said second and third threshold;

a pulse generator that generates one of a first type and a second type of therapeutic pulses for the heart in accordance with a first and a second command signal, respectively; said first type of therapeutic pulses defining an antitachycardia therapy consisting of low level cardioversion pacing pulses, and said second type of therapeutic pulses defining a shock therapy consisting of high level defibrillation shock pulses;

a therapy selector that monitors said intrinsic ventricular, said selector including a stability detector to determine if the ventricle is stable when said intrinsic ventricular rate is in said intermediate rate range;

wherein said therapy selector generates said first command signal when said intrinsic ventricular rate is within said fast rate and when said intrinsic ventricular rate is in said intermediate range and the ventricle is stable; and wherein said therapy selector generates said second command if said intrinsic ventricular rate is in said very fast range and when said intrinsic ventricular rate is in said intermediate range and the ventricle is unstable.

9. The device of claim 8 wherein said stability detector analyzes said ventricle for several past ventricular intrinsic beats.

10. The device of claim 8 wherein said stability detector generates a stability value and wherein said stability detector further includes a comparator that compares said stability value to a threshold level to determine if the ventricle is stable.

11. The device of claim 8 wherein said stability detector includes a calculator that calculates a variability of said intrinsic ventricular rate over a predetermined period.

12. A method of providing antitachycardia therapy to a patient's heart using an implantable cardiac device, said method comprising:

detecting an intrinsic ventricular parameter of the heart;

determining if said intrinsic ventricular parameter corresponds to one of a fast rate range, an intermediate rate range higher than said fast rate range and a very fast rate range higher than said intermediate rate range;

if said parameter corresponds to said intermediate rate range, determining if the ventricle is stable;

applying a low level antitachycardia therapy if said intrinsic ventricular parameter corresponds to said fast rate range;

applying said low level antitachycardia therapy if said intrinsic ventricular parameter corresponds to said intermediate rate range and said ventricle is stable;

applying a high level antitachycardia therapy if said intrinsic ventricular parameter corresponds to said intermediate rate range and said ventricle is unstable; and applying said high level antitachycardia therapy if said intrinsic ventricular parameter corresponds to said very fast rate range.

13. The method of claim 12 wherein said low level antitachycardia therapy comprises a plurality of cardioversion pacing pulses selected to cardiovert said ventricle to a normal sinus rhythm.

14. The method of claim 12 wherein said high level antitachycardia therapy includes applying a plurality of high energy defibrillation shock pulses.

15. The method of claim 12 wherein said step of determining if said ventricle is stable includes monitoring said intrinsic ventricular parameter for a predetermined time period.

16. The method of claim 15 wherein said step of monitoring includes calculating a variability of said intrinsic ventricular parameter.

17. The method of claim 16 wherein said monitoring further includes comparing said variability to a threshold value, wherein said ventricle is determined to be stable if said variability is below said threshold value.

* * * * *